(12) United States Patent
Zhong et al.

(10) Patent No.: US 12,378,210 B2
(45) Date of Patent: Aug. 5, 2025

(54) PHARMACEUTICAL COMPOSITION COMPRISING TIZOXANIDE AND PHARMACEUTICAL USE THEREOF

(71) Applicant: BEIJING JUNKE HUAYUAN MED TECH CO., LTD., Beijing (CN)

(72) Inventors: Bohua Zhong, Beijing (CN); Ming Zhou, Beijing (CN); Hongwu Li, Beijing (CN)

(73) Assignee: BEIJING JUNKE HUAYUAN MED TECH CO., LTD., Beijing (CN)

( * ) Notice: Subject to any disclaimer, the term of this patent is extended or adjusted under 35 U.S.C. 154(b) by 547 days.

(21) Appl. No.: 17/906,505

(22) PCT Filed: Mar. 12, 2021

(86) PCT No.: PCT/CN2021/080327
§ 371 (c)(1),
(2) Date: Sep. 16, 2022

(87) PCT Pub. No.: WO2021/185154
PCT Pub. Date: Sep. 23, 2021

(65) Prior Publication Data
US 2023/0150959 A1    May 18, 2023

(30) Foreign Application Priority Data
Mar. 16, 2020 (CN) .......... 202010185575.0

(51) Int. Cl.
*A61P 31/16* (2006.01)
*A61P 31/20* (2006.01)
*C07C 215/40* (2006.01)
*C07D 277/58* (2006.01)

(52) U.S. Cl.
CPC ............ *C07D 277/58* (2013.01); *A61P 31/16* (2018.01); *A61P 31/20* (2018.01); *C07C 215/40* (2013.01); *C07B 2200/13* (2013.01)

(58) Field of Classification Search
CPC .. C07C 215/40; C07D 277/58; C07B 2200/13
See application file for complete search history.

(56) References Cited

FOREIGN PATENT DOCUMENTS

| CN | 103648282 A | 3/2014 | |
|---|---|---|---|
| CN | 104277012 A | 1/2015 | |
| CN | 105777808 A | 7/2016 | |
| CN | 109069648 A | 12/2018 | |
| EP | 3078377 A2 | 10/2016 | |
| WO | WO-2022020243 A1 * | 1/2022 | .............. A61P 31/12 |

OTHER PUBLICATIONS

Lin, Ning et al.; "Method of promotion of oral drug absorption", Biopharmaceuticals and Pharmacokinetics; Mar. 31, 2011; pp. 37-38.

* cited by examiner

*Primary Examiner* — Amanda L. Aguirre
(74) *Attorney, Agent, or Firm* — NKL Law; Allen Xue

(57) ABSTRACT

A pharmaceutical composition contains tizoxanide and choline hydroxide, a choline salt of tizoxanide and crystal form thereof. A mixture of tizoxanide and choline hydroxide, or a salt thereof and crystal form of the salt significantly improve the solubility and bioavailability of tizoxanide, and exhibits favorable effects in drugs for treating viruses, fibrosis, bacteria, tumors and intestinal parasites.

15 Claims, 1 Drawing Sheet

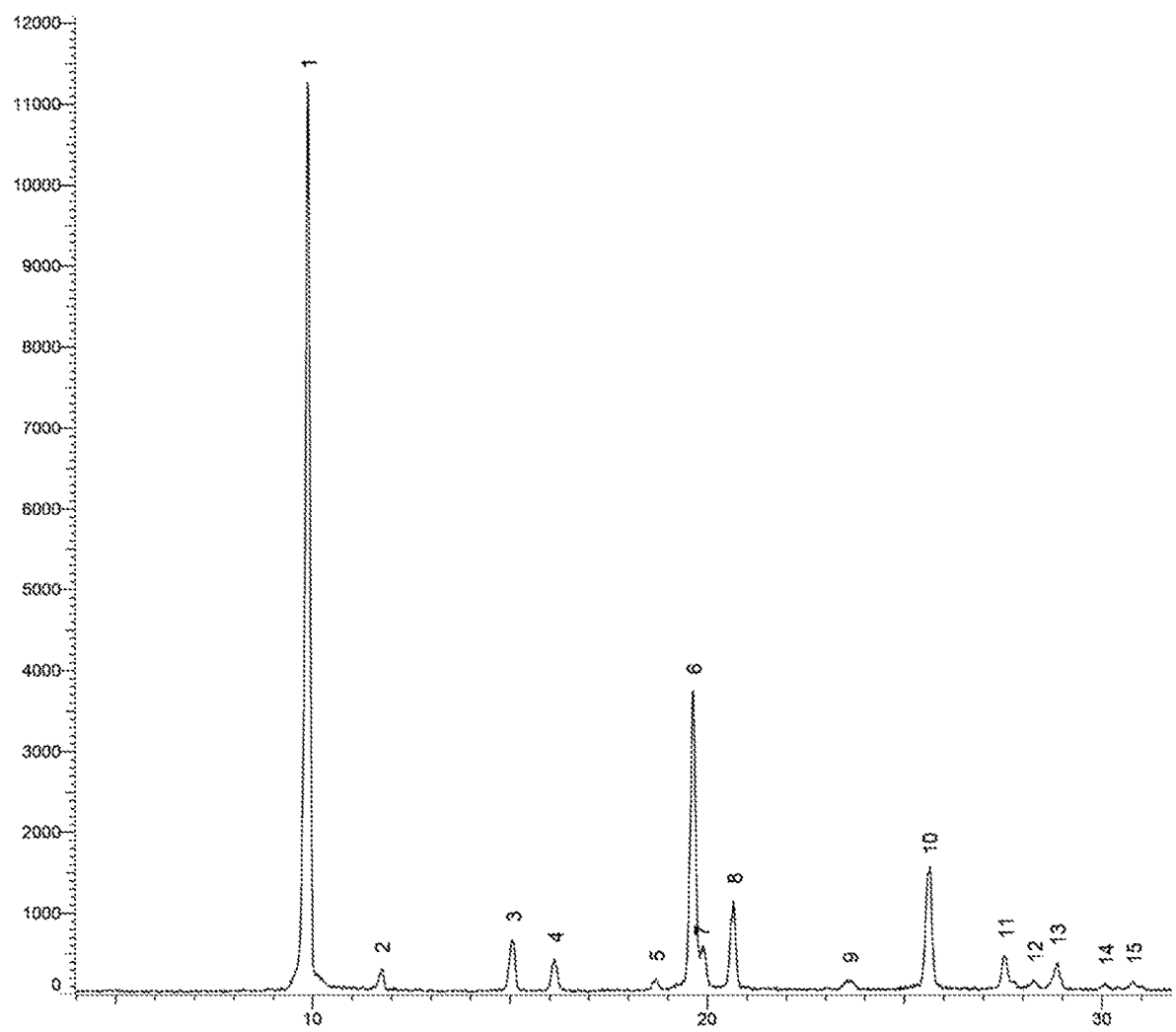

PHARMACEUTICAL COMPOSITION COMPRISING TIZOXANIDE AND PHARMACEUTICAL USE THEREOF

CROSS-REFERENCE TO RELATED APPLICATIONS

This application is a U.S. national stage entry of PCT International Application No. PCT/CN2021/080327, filed on Mar. 12, 2021, which claims the priority to Chinese Patent Application No. 202010185575.0 filed on Mar. 16, 2020, with China National Intellectual Property Administration, entitled "PHARMACEUTICAL COMPOSITION COMPRISING TIZOXANIDE AND PHARMACEUTICAL USE THEREOF", the content of which is incorporated herein by reference in its entirety.

TECHNICAL FIELD

The present disclosure relates to a pharmaceutical composition comprising tizoxanide and the pharmaceutical use thereof, and specifically relates to a pharmaceutical composition containing tizoxanide and choline and the pharmaceutical use thereof.

BACKGROUND

Nitazoxanide (chemical name: o-N-(5-nitrothiazol-2-yl) carbamoyl-phenol-acetate) is a nitrothiazolyl-salicylamide derivative, and has the drug effects of resisting protozoans, intestinal parasites, bacteria, etc.

Further researches showed that nitazoxanide also has broad-spectrum antiviral activity (Rossignol J F., *Antiviral Research*, 2014; 110: 94-103), and has an inhibitory effect on influenza A virus, influenza B virus, avian influenza, respiratory syncytial virus, parainfluenza virus, coronavirus, rotavirus, norovirus, hepatitis B virus, hepatitis C virus, dengue fever virus, yellow fever virus, encephalitis B virus, human immunodeficiency virus, etc.

Nitazoxanide also has a good inhibitory effect on *Tubercle bacillus* (Ranjbar S, et al., *iScience*, 2019; 22: 299-313) and *Helicobacter pylori* (Basu P P, et al., *Am J Gastroenterol*, 2011; 106: 1970-1975).

The Chinese Patent Application (CN109069648A) discloses use of nitazoxanide for treating bile stasis and fibrosis diseases, the fibrosis diseases comprising hepatic fibrosis, pulmonary fibrosis, etc.

Nitazoxanide also has an anti-tumor effect (Di Santo N and Ehrisman J., *Mutation Research*, 2014; 768: 16-21), and has a strong inhibitory effect on both ovarian cancer (Di Santo N and Ehrisman J., *Cancers*, 2013; 5: 1163-1176) and colon cancer (Senkowski W, Zhang X, et al., *Mol Cancer Ther*, 2015; 14: 1504-1516).

However, as with most of the old drugs with promising new use, the clinical efficacy of these new pharmacological actions of nitazoxanide still needs to be improved. Nitazoxanide hardly dissolve in water (solubility of which in water is 0.000189 mg/mL), large in dosage (500 mg/time, 2 times/day) and low in oral bioavailability, and can hardly reach effective antiviral concentration in lung, so that its treatment effect through oral administration on respiratory virus infection is limited.

How to improve the efficacy of an old drug becomes a bottleneck restricting the use of the old drug to exerting a new drug effect.

Nitazoxanide, after oral administration, is converted in vivo to the active metabolite Tizoxanide and the inactive metabolite glucuronic acid conjugate:

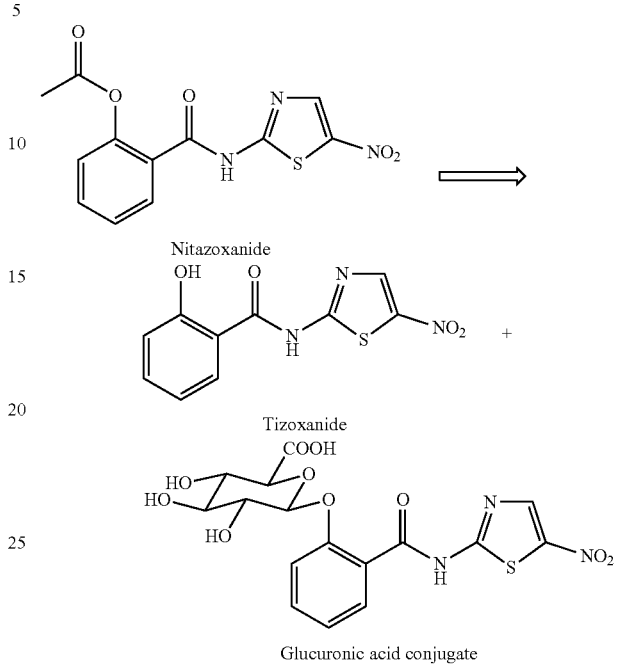

After oral administration of nitazoxanide in human, the original form of nitazoxanide is undetectable in blood, and only the conjugate of tizoxanide and glucuronic acid can be detected, the systemic exposure of the glucuronic acid conjugate being higher than that of tizoxanide.

SUMMARY

The present disclosure provides a pharmaceutical composition containing tizoxanide and choline hydroxide.

According to an embodiment of the present disclosure, the molar ratio of tizoxanide to choline hydroxide in the pharmaceutical composition is 1:4 to 1:0.25.

Preferably, the molar ratio of tizoxanide to choline hydroxide in the pharmaceutical composition is 1:2 to 1:0.5.

For example, the molar ratio of tizoxanide to choline hydroxide is 1:1, 1:0.5, 1:0.25, 1:2, 1:3 or 1:4.

According to an embodiment of the present disclosure, tizoxanide and choline hydroxide form a salt in a molar ratio of 1:1.

According to an exemplary embodiment of the present disclosure, the pharmaceutical composition contains a tizoxanide choline salt of formula (I):

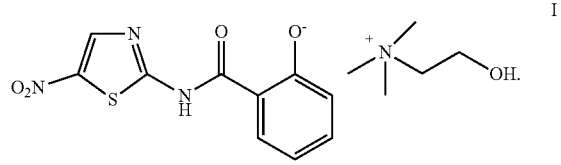

The present disclosure further provides the tizoxanide choline salt of formula (I) described above.

According to an embodiment of the present disclosure, the tizoxanide choline salt of formula (I) may be in an amorphous form or in a crystalline form, and preferably in a crystalline form.

The present disclosure further provides a crystalline form of the tizoxanide choline salt of formula (I) described above.

According to an embodiment of the present disclosure, the tizoxanide choline salt of formula (I) is in a crystalline form having characteristic peaks at the following 2θ angles (°) in a powder X-ray diffraction pattern obtained using Cu-Kα radiation: 9.92±0.10, 15.10±0.10, 19.72±0.10, 20.69±0.10 and 25.66±0.10, wherein the peak at 9.92±0.10 is the strongest peak.

According to an embodiment of the present disclosure, the tizoxanide choline salt of formula (I) is in a crystalline form having characteristic peaks at the following 2θ angles (°) in a powder X-ray diffraction pattern obtained using Cu-Kα radiation: 9.92±0.10, 15.10±0.10, 16.16±0.10, 19.72±0.10, 19.88±0.10, 20.69±0.10, 25.66±0.10 and 27.59±0.10, wherein the peak at 9.92±0.10 is the strongest peak.

Preferably, the tizoxanide choline salt of formula (I) is in a crystalline form having characteristic peaks at the following 2θ angles (°) in a powder X-ray diffraction pattern obtained using Cu-Kα radiation: 9.92±0.10, 11.78±0.10, 15.10±0.10, 16.16±0.10, 19.72±0.10, 19.88±0.10, 20.69±0.10, 25.66±0.10, 27.59±0.10 and 28.88±0.10, wherein the peak at 9.92±0.10 is the strongest peak.

According to an embodiment of the present disclosure, the tizoxanide choline salt of formula (I) has a powder X-ray diffraction pattern substantially as shown in the FIGURE.

According to an embodiment of the present disclosure, the pharmaceutical composition also comprises a non-toxic pharmaceutically acceptable pharmaceutical carrier or excipient.

Preferably, the pharmaceutical composition is a pharmaceutical composition containing tizoxanide and choline, and a non-toxic pharmaceutically acceptable pharmaceutical carrier or excipient.

According to an embodiment of the present disclosure, the pharmaceutical composition may be a capsule, a tablet, a granule, a powder, a suspension, a solution formulation or a lozenge.

According to an embodiment of the present disclosure, the pharmaceutical composition may be administered by an oral or injectable route.

The present disclosure provides use of the tizoxanide choline salt of formula (I) described above, the crystalline form of the tizoxanide choline salt of formula (I) described above, or the pharmaceutical composition described above for the manufacturing of an antiviral medicament.

Preferably, the antiviral medicament may be an anti-hepatitis virus medicament and/or an anti-respiratory virus medicament.

Preferably, the anti-hepatitis virus medicament may be an anti-hepatitis B virus medicament and/or an anti-hepatitis C virus medicament.

Preferably, the anti-respiratory virus medicament may be an anti-influenza virus medicament and/or an anti-coronavirus medicament.

The present disclosure further provides use of the tizoxanide choline salt of formula (I) described above, the crystalline form of the tizoxanide choline salt of formula (I) described above, or the pharmaceutical composition described above for the manufacturing of an anti-fibrosis medicament.

Preferably, the anti-fibrosis medicament may be an anti-hepatic fibrosis medicament and/or an anti-pulmonary fibrosis medicament.

The present disclosure further provides use of the tizoxanide choline salt of formula (I) described above, the crystalline form of the tizoxanide choline salt of formula (I) described above, or the pharmaceutical composition described above for the manufacturing of an antibacterial medicament.

Preferably, the antibacterial medicament may be an anti-*Helicobacter pylori* medicament and/or an anti-*Tubercle bacillus* medicament.

The present disclosure further provides use of the tizoxanide choline salt of formula (I) described above, the crystalline form of the tizoxanide choline salt of formula (I) described above, or the pharmaceutical composition described above for the manufacturing of an anti-tumor medicament.

Preferably, the anti-tumor medicament may be an anti-ovarian cancer medicament and/or an anti-colon cancer medicament.

The present disclosure further provides use of the tizoxanide choline salt of formula (I) described above, the crystalline form of the tizoxanide choline salt of formula (I) described above, or the pharmaceutical composition described above for the manufacturing of an anti-parasitic medicament.

Preferably, the anti-intestinal parasite medicament may be an anti-*Cryptosporidium parvum* medicament and/or an anti-*Giardia lamblia* medicament.

The present disclosure further provides the tizoxanide choline salt of formula (I) described above, the crystalline form of the tizoxanide choline salt of formula (I) described above or the pharmaceutical composition described above for use in treating diseases such as viral infection, fibrosis diseases, bacterial infection, cancer, parasitic infection and the like in a patient.

According to an embodiment of the present disclosure, the viral infection may be hepatitis viral infection or respiratory viral infection. Preferably, the hepatitis virus may be hepatitis B virus or hepatitis C virus. Preferably, the respiratory virus may be an influenza virus or a coronavirus.

According to an embodiment of the present disclosure, the fibrosis disease may be hepatic fibrosis and/or pulmonary fibrosis.

According to an embodiment of the present disclosure, the bacterial infection may be *Helicobacter pylori* infection and/or *Tubercle bacillus* infection.

According to an embodiment of the present disclosure, the cancer may be ovarian cancer or colon cancer.

According to an embodiment of the present disclosure, the parasitic infection may be *Cryptosporidium parvum* infection and/or anti-*Giardia lamblia* infection.

The present disclosure further provides a method for treating a viral infectious disease, which comprises the following step: administering to a patient or subject in need thereof a therapeutically effective amount of the tizoxanide choline salt of formula (I) described above, the crystalline form of the tizoxanide choline salt of formula (I) described above, or the pharmaceutical composition described above.

According to an embodiment of the present disclosure, the viral infectious disease may be hepatitis virus infection or respiratory virus infection. Preferably, the hepatitis virus may be hepatitis B virus or hepatitis C virus. Preferably, the respiratory virus may be an influenza virus or a coronavirus.

The present disclosure further provides a method for treating a fibrosis disease, which comprises the following step: administering to a patient or subject in need thereof a therapeutically effective amount of the tizoxanide choline salt of formula (I) described above, the crystalline form of the tizoxanide choline salt of formula (I) described above, or the pharmaceutical composition described above.

According to an embodiment of the present disclosure, the fibrosis disease may be hepatic fibrosis and/or pulmonary fibrosis.

The present disclosure further provides a method for treating a bacterial infectious disease, which comprises the following step: administering to a patient or subject in need thereof a therapeutically effective amount of the tizoxanide choline salt of formula (I) described above, the crystalline form of the tizoxanide choline salt of formula (I) described above, or the pharmaceutical composition described above.

According to an embodiment of the present disclosure, the bacterial infectious disease may be *Helicobacter pylori* infection and/or *Tubercle bacillus* infection.

The present disclosure further provides a method for treating cancer, which comprises the following step: administering to a patient or subject in need thereof a therapeutically effective amount of the tizoxanide choline salt of formula (I) described above, the crystalline form of the tizoxanide choline salt of formula (I) described above, or the pharmaceutical composition described above.

According to an embodiment of the present disclosure, the cancer may be ovarian cancer and/or colon cancer.

The present disclosure further provides a method for treating a parasitic infectious disease, which comprises the following step: administering to a patient or subject in need thereof a therapeutically effective amount of the tizoxanide choline salt of formula (I) described above, the crystalline form of the tizoxanide choline salt of formula (I) described above, or the pharmaceutical composition described above.

According to an embodiment of the present disclosure, the parasitic infection may be *Cryptosporidium parvum* infection and/or anti-*Giardia lamblia* infection.

Beneficial Effects of Present Disclosure

The present disclosure has surprisingly found that tizoxanide and a certain proportion of choline hydroxide can form a mixture which can significantly improve the solubility and bioavailability of tizoxanide. In particular, tizoxanide and choline hydroxide can form a salt in a molar ratio of 1:1 which may also significantly improve the solubility and bioavailability of tizoxanide. In addition, the mixture, the salt and the crystalline form of the salt, and the pharmaceutical composition containing the same have good effects on antiviral, anti-fibrosis, antibacterial, anti-tumor and/or anti-intestinal parasite medicaments.

BRIEF DESCRIPTION OF THE DRAWINGS

The FIGURE shows a powder X-ray diffraction pattern of tizoxanide choline salt of formula (I) determined in Example 3, wherein the abscissa is 2θ angles (°) and the ordinate is the intensity of the absorption peak.

DETAILED DESCRIPTION

The technical solutions of the present disclosure will be further illustrated in detail with reference to the following specific examples. It should be understood that the following examples are merely exemplary illustration and explanation of the present disclosure, and should not be construed as limiting the protection scope of the present disclosure. All techniques implemented based on the content of the present disclosure described above are encompassed within the protection scope of the present disclosure.

Unless otherwise stated, the starting materials and reagents used in the following examples are all commercially available products or can be prepared by known methods.

Unless otherwise specified, "%" in the examples is defined as mass percentage.

The tizoxanide choline salt of formula (I) can be prepared according to the following synthetic route:

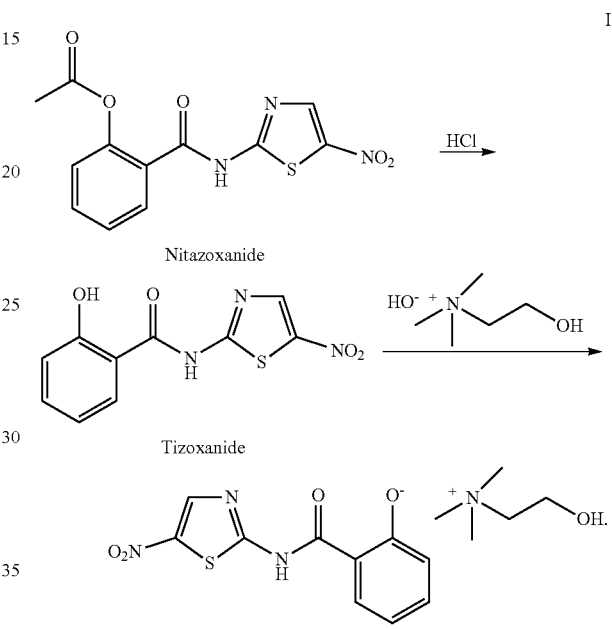

Nitazoxanide is hydrolyzed under the action of hydrochloric acid to remove acetyl to obtain deacetylated nitazoxanide, namely tizoxanide; tizoxanide is reacted with choline hydroxide to obtain the tizoxanide choline salt of formula (I).

Example 1: Preparation of Tizoxanide

To a 500 mL three-necked flask was added 300 mL of concentrated hydrochloric acid, followed by addition of 50 g of nitazoxanide under stirring; after the addition was completed, the reaction mixture was stirred and reacted at 50° C. for 20 h, cooled to room temperature, and filtered, and the filter cake was washed with a small amount of water and acetone in sequence, filtered under suction to dryness, and dried at 45° C. to obtain 42.6 g of light yellow powder, namely tizoxanide.

Example 2: Preparation of Tizoxanide Choline Salt of Formula (I)

To a 1000 mL three-necked flask was added 500 mL of methanol, followed by addition of 50 g of tizoxanide under stirring, and the mixture was stirred homogeneously; the reaction mixture was stirred at room temperature, and added dropwise with 57.2 g of 40% aqueous choline hydroxide solution; after the addition was completed, the system was warmed to 45° C. and stirred and reacted for 1 h, and filtered while hot. The filtrate was placed at −5° C. overnight and then filtered. The filter cake was rinsed with 100 mL of methanol, filtered under suction to dryness, and dried to obtain 49.03 g of yellow crystalline powder (purity: 98%), namely the tizoxanide choline salt of formula (I). δ (ppm, DMSO-$d_6$, 600 MHz) of the tizoxanide choline salt of formula (I) in $^1$H NMR spectroscopy: 3.10 (9H, s); 3.38-3.40 (2H, dd); 3.81-3.85 (2H, m); 5.26-5.27 (1H, t); 6.79-6.82 (2H, m); 7.29-7.32 (1H, m); 7.90-7.91 (1H, m); 8.50 (1H, s); 14.70 (1H, s).

Example 3: Characterization of Crystalline Form

The crystalline form of tizoxanide choline salt of formula (I) prepared in Example 2 was characterized by powder X-ray diffraction.

Test conditions and method for powder X-ray diffraction were as follows: the instrument model was DMAX-2500; the experimental method was as follows: the test sample was ground into 200-300 meshes, with the scanning angle range being 3.0-60.0 degrees and the scanning rate being 0.15 degree/second for counting.

The FIGURE showed a powder X-ray diffraction pattern of tizoxanide choline salt of formula (I), wherein the abscissa was 2θ angles and the ordinate was the intensity of the absorption peak. The characterization results were as follows: the tizoxanide choline salt of formula (I) had characteristic peaks at the following 2θ angles (°) in the X-ray powder diffraction pattern: 9.92±0.10, 11.78±0.10, 15.10±0.10, 16.16±0.10, 19.72±0.10, 19.88±0.10, 20.69±0.10, 25.66±0.10, 27.59±0.10 and 28.88±0.10, wherein the peak at 9.92±0.10 was the strongest peak.

Example 4: Pharmacokinetic Evaluation of Drug in Rat by Oral Administration 34.75 mg of nitazoxanide was added to 10 mL of 0.5% sodium carboxymethylcellulose solution, and the mixture was mixing homogeneously for later use;

41.67 mg of tizoxanide choline salt of formula (I) prepared in Example 2 was added to 10 mL of 0.5% sodium carboxymethylcellulose solution, and the mixture was mixed homogeneously for later use;

30 mg of tizoxanide was added to 5 mL of 0.5% sodium carboxymethylcellulose solution, followed by addition of 40% aqueous choline hydroxide solution, and the mixture was mixed homogeneously, and then added with 0.5% sodium carboxymethyl cellulose solution to a final volume of 10 mL to obtain a mixture of tizoxanide and choline for later use. The addition amount of the aqueous choline hydroxide solution was adjusted to obtain mixtures of tizoxanide and choline with molar ratios of tizoxanide to choline hydroxide of 1:2, 1:0.5 and 1:1, respectively.

Provided were male SD rats weighing 180 g to 220 g, 3 rats each group; all animals were fasted for 12 h prior to administration. The rats were separately administered intragastrically with the solution of the nitazoxanide, the solution of the tizoxanide choline salt of formula (I) or the mixture of tizoxanide and choline described above at a dose of 10 mL/kg each. Blood was collected via jugular veins at 0.2 mL/time prior to administration and 15 min, 30 min, 1 h, 2 h, 4 h, 6 h, 8 h and 24 h after administration. The collected blood was added with sodium heparin for anticoagulation, followed by centrifugation to separate plasma, and the plasma was storing at −80° C. for determination. The content of tizoxanide in plasma was determined by LC-MS/MS (instrument: LC-MS/MS-19, TQ5500 Triple quad); internal Standard (IS) was tolbutamide; mass spectrum conditions: an electrospray ion source and a negative ion multiple reaction detection (Tizoxanide: Q1/Q3 Masses: 263.80/217.00 Da, and internal standard: Q1/Q3 Masses: 269.20/106.10 Da); liquid phase chromatography conditions: mobile phase A was 0.3% aqueous formic acid solution, and mobile phase B was 0.1% formic acid in acetonitrile; chromatographic column: ACQUITY UPLC CORTECS T3, 2.7 μm (2.1×100 mm); column temperature was 40° C.; flow rate was 0.6 mL/min.

The pharmacokinetic parameters were calculated by utilizing WinNonlin according to the plasma concentration data at different time points. The results are shown in Table 1:

TABLE 1

Results of pharmacokinetic evaluation of drug in rat by oral administration

| Group | $T_{1/2}$ (h) | $T_{max}$ (h) | $C_{max}$ (ng/mL) | $AUC_{(0-t)}$ (h*ng/mL) | $AUC_{(0-\infty)}$ (h*ng/mL) |
|---|---|---|---|---|---|
| Nitazoxanide | 0.65 | 2.00 | 380.55 | 1325.50 | 1327.91 |
| Mixture of tizoxanide + choline (molar ratio 1:2) | 0.69 | 1.00 | 909.94 | 2490.09 | 2492.64 |
| Mixture of tizoxanide + choline (molar ratio 1:0.5) | 1.10 | 2.33 | 587.30 | 1739.98 | 1741.39 |
| Mixture of tizoxanide + choline (molar ratio 1:1) | 1.68 | 1.08 | 602.42 | 2478.67 | 2197.56 |
| Tizoxanide choline salt of formula (I) | 2.53 | 0.25 | 837.16 | 2070.01 | 2280.30 |

Example 5: Evaluation of In Vivo Anti-Hepatitis B Virus Effect

The shed ducks (Tadorna) with vertical transmission infection and positive DHBV DNA were randomly grouped, 8 shed ducks each group. The test compounds, i.e., the tizoxanide choline salt of formula (I) prepared in Example 2 and nitazoxanide, were each formulated into suspensions with 0.1% sodium carboxymethylcellulose, and administered intragastrically once every day. Blood was collected intravenously prior to administration ($T_0$) and 7 days ($T_7$), 14 days ($T_{14}$), 21 days ($T_{21}$) and 28 days ($T_{28}$) after administration, and the serum was separated and frozen at −70° C. for determination.

Determination of DHBV DNA content in serum by using dot-blot molecular hybridization was as follows: the duck serum described above was taken, spots were simultaneously formed on detection films for each batch, the change of the DHBV DNA level in the duck serum was determined, the DHBV DNA probe was labeled by $^{32}$P according to the method of the instruction of the nick translation kit, and a duck serum dot-blot experiment was performed. After the autoradiography, the spectral absorbance (filter wavelength was 490 nm) $OD_{490}$ of the spots on the autoradiography X-film was determined with an enzyme-linked immunoassay instrument, a higher $OD_{490}$ value indicates a higher virus content.

The determination results are shown in Table 2:

TABLE 2

Results of evaluation of in vivo anti-hepatitis B virus effect

| Group | Dose (mg/kg, active ingredient basis) | $OD_{490}$ value | | | | |
|---|---|---|---|---|---|---|
| | | $T_0$ | $T_7$ | $T_{14}$ | $T_{21}$ | $T_{28}$ |
| Vehicle group | | 1.59 ± 0.17 | 1.62 ± 0.14 | 1.73 ± 0.20 | 1.86 ± 0.60 | 1.83 ± 0.23 |
| Tizoxanide | 200 | 0.96 ± 0.47 | 0.15 ± 0.08ΔΔ | 0.10 ± 0.05ΔΔ | 0.07 ± 0.04ΔΔ | 0.27 ± 0.17ΔΔ |
| choline salt of formula (I) | 100 | 1.47 ± 0.20 | 0.43 ± 0.18ΔΔ | 0.39 ± 0.34ΔΔ | 0.34 ± 0.25ΔΔ | 0.53 ± 0.37ΔΔ |
| Nitazoxanide | 200 | 1.67 ± 0.11 | 1.37 ± 0.27 | 1.19 ± 0.51 | 0.72 ± 0.38ΔΔ | 0.72 ± 0.48ΔΔ |

Note:
the drug groups administered at different time points were compared with those groups prior to administration ($T_0$): **P < 0.01, *P < 0.05;
The drug groups and the control group were compared at the same time points of administration: ΔΔP < 0.01, ΔP < 0.05.

Example 6: Evaluation of Anti-Influenza Virus Effect in Mouse Model

Male Kunming mice weighing 18 g to 22 g were randomly divided into a normal group, a model group and an administration group, 10 mice each group. The mice in the model group and the administration group were infected with influenza A virus mouse lung adaptive strain A/PR/8/34 via nasal instillation at 10 folds of $LD_{50}$ dose; the test compounds, i.e., nitazoxanide and the tizoxanide choline salt of formula (I) prepared in Example 2, were each formulated as suspensions with 0.1% sodium carboxymethylcellulose, and administered intragastrically 1 hour after infection, 2 times every day, for 5 consecutive days. The mice were observed for mortality and recorded for 14 consecutive days for examination of their survival rates.

The experimental results are shown in Table 3:

TABLE 3

Protective effect of target compounds on influenza virus infected mice

| Drug | Dose (mg/kg, active ingredient basis) | Survival rates (%) |
|---|---|---|
| Normal group | 0 | 10/10 |
| Nitazoxanide | 100 | 7/10 |
| | 50 | 2/10 |
| Tizoxanide choline salt of formula (I) | 50 | 9/10 |
| | 25 | 3/10 |

The embodiments of the present disclosure have been described above. However, the present disclosure is not limited thereto. Any modification, equivalent, improvement and the like made without departing from the spirit and principle of the present disclosure shall fall within the protection scope of the present disclosure.

The invention claimed is:

1. A pharmaceutical composition, containing tizoxanide and choline hydroxide.

2. The pharmaceutical composition as claimed in claim 1, wherein tizoxanide and choline hydroxide are in a molar ratio of 1:4 to 1:0.25.

3. The pharmaceutical composition as claimed in claim 1, wherein tizoxanide and choline hydroxide are in a molar ratio of 1:1 to form a tizoxanide choline salt of formula (I):

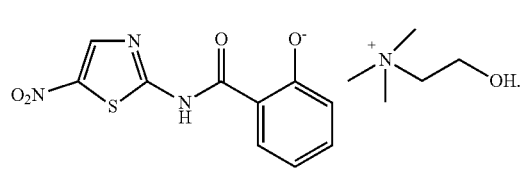

4. The pharmaceutical composition as claimed in claim 3, wherein the tizoxanide choline salt of formula (I) is in an amorphous form or a crystalline form.

5. The pharmaceutical composition as claimed in claim 1, wherein the pharmaceutical composition further comprises a non-toxic pharmaceutically acceptable pharmaceutical carrier or excipient.

6. A medicament comprising the pharmaceutical composition of claim 1, wherein the medicament is effective in inhibiting growth of hepatitis virus, respiratory virus, bacteria, tumor, fibrosis, and/or intestinal parasite.

7. The medicament of claim 6, wherein the hepatitis virus is a hepatitis B virus or a hepatitis C virus, the respiratory virus is influenza virus or coronavirus, the bacteria is *Helicobacter pylori* or *Tubercle bacillus*, the tumor is ovarian cancer or colon cancer, the fibrosis is hepatic fibrosis or pulmonary fibrosis, and the intestinal parasite is *Cryptosporidium parvum* or *Giardia lamblia*.

8. A tizoxanide choline salt of formula (I),

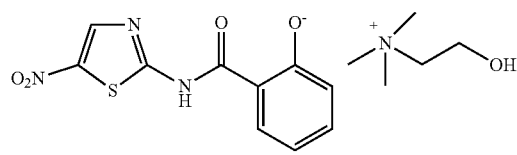

9. The tizoxanide choline salt as claimed in claim 8, wherein the tizoxanide choline salt of formula (I) is in a crystalline form having characteristic peaks at the following 2θ angles (°) in a powder X-ray diffraction pattern obtained using Cu-Kα radiation: 9.92±0.10, 15.10±0.10, 19.72±0.10, 20.69±0.10 and 25.66±0.10, wherein the peak at 9.92±0.10 is the strongest peak.

10. The tizoxanide choline salt as claimed in claim 8, wherein the tizoxanide choline salt of formula (I) is in an amorphous form.

11. A medicament comprising the tizoxanide choline salt of formula (I) of claim 8.

12. The medicament of claim 11, wherein the hepatitis virus is a hepatitis B virus or a hepatitis C virus, the respiratory virus is influenza virus or coronavirus, the bacteria is *Helicobacter pylori* or *Tubercle bacillus*, the tumor is ovarian cancer or colon cancer, the fibrosis is hepatic fibrosis or pulmonary fibrosis, and the intestinal parasite is *Cryptosporidium parvum* or *Giardia lamblia*.

13. A crystalline form of a tizoxanide choline salt of formula (I),

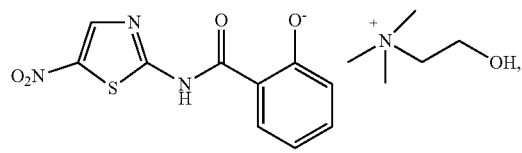

wherein the crystalline form has characteristic peaks at the following 2θ angles (°) in a powder X-ray diffraction pattern obtained using Cu-Kα radiation: 9.92±0.10, 15.10±0.10, 16.16±0.10, 19.72±0.10, 19.88±0.10, 20.69±0.10, 25.66±0.10 and 27.59±0.10, wherein the peak at 9.92±0.10 is the strongest peak.

14. A medicament comprising the crystalline form of the tizoxanide choline salt of formula (I) of claim 13.

15. The medicament of claim 11, wherein the hepatitis virus is a hepatitis B virus or a hepatitis C virus, the respiratory virus is influenza virus or coronavirus, the bacteria is *Helicobacter pylori* or *Tubercle bacillus*, the tumor is ovarian cancer or colon cancer, the fibrosis is hepatic fibrosis or pulmonary fibrosis, and the intestinal parasite is *Cryptosporidium parvum* or *Giardia lamblia*.

* * * * *